United States Patent [19]

Fulmer

[11] Patent Number: 4,480,134

[45] Date of Patent: Oct. 30, 1984

[54] PROCESS FOR PREPARING PHENOL AND ACETONE FROM CUMENE

[75] Inventor: John W. Fulmer, Mt. Vernon, Ind.

[73] Assignee: General Electric Company, Mt. Vernon, Ind.

[21] Appl. No.: 482,298

[22] Filed: Apr. 5, 1983

[51] Int. Cl.$^3$ ............................................. C07C 45/53
[52] U.S. Cl. ..................................... 568/385; 568/798
[58] Field of Search .............................. 568/385, 798

[56] References Cited

U.S. PATENT DOCUMENTS

| | | | |
|---|---|---|---|
| 2,715,145 | 8/1955 | Bewley et al. | 568/385 |
| 2,728,795 | 12/1955 | Armstrong et al. | 568/385 |
| 2,737,480 | 3/1956 | Adams et al. | 568/385 |
| 2,781,222 | 4/1959 | Joris et al. | 568/385 |
| 2,904,592 | 9/1959 | Ellis et al. | 568/385 |
| 2,906,789 | 9/1959 | McNaughton | 568/385 |
| 2,957,921 | 10/1960 | Adams et al. | 568/385 |
| 2,986,583 | 5/1961 | Robbers et al. | 568/385 |
| 3,215,745 | 11/1965 | Frank | 568/385 |
| 4,271,322 | 6/1981 | Matsunaga et al. | 568/798 |
| 4,351,967 | 9/1982 | Nishimura et al. | 568/798 |

Primary Examiner—James H. Reamer
Attorney, Agent, or Firm—Martin B. Barancik

[57] ABSTRACT

Benzene is removed from the heavy residues of a phenol distillation in a phenol and acetone from cumene process.

8 Claims, 2 Drawing Figures

PROCESS FOR PREPARING PHENOL AND ACETONE FROM CUMENE

BACKGROUND OF THE INVENTION

Phenol is a basic commodity chemical with many end uses. Most of the phenol manufactured is prepared from isopropyl benzene, hereafter referred to as cumene. The reaction sequence is short and entails the following steps:

1. Air oxidation of cumene to give cumene hydroperoxide.

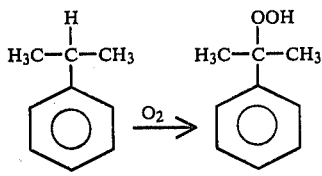

2. Acid cleavage of the hydroperoxide to provide phenol and acetone.

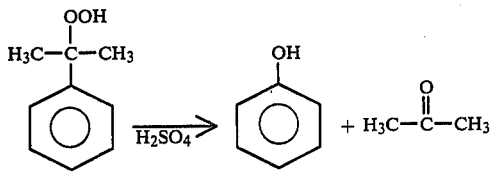

The phenol and acetone are separated and each one purified to the degree necessary to satisfy its ultimate use. As is readily observed, for every mole of phenol that is produced, a mole of acetone is also theoretically produced. Acetone is also a commodity chemical with various end uses. Although not shown in the schematic equations, there are by-products formed as well which must be removed to various degrees depending upon the end use of the phenol or acetone. Additionally other by-products are formed by various concentrating methods and processing conditions utilized after the cleavage of the cumene hydroperoxide. The by-products include dimethylbenzyl alcohol, α-methylstyrene, cumylphenol, mesityl oxide, hydroxy acetone, benzene, toluene, dimers and higher polymers of various components including α-methylstyrene.

Various of these heavier tar like materials, for example the above mentioned polymers, generally known as "heavy ends" are removed as residues from the bottoms of a distillation tower utilized to purify the phenol. Since many of these "heavy ends" are made from products desirable for recycle such as cumene and α-methylstyrene, as well as cumyl phenol, it has become part of the general processing steps of phenol manufacture to break down these heavy ends through, for example, a heat treatment, "cracking", to their individual desirable compounds such as cumene. These compounds are then recycled into the process streams thereby increasing the overall conversion of the process. However in accomplishing this desirable effect, the heat treatment also produced other products which had undesirable effects on product purity when introduced into the process streams on recycle. The production of these undesirable compounds by the heat treatment has not been appreciated to date. Specifically the cracking of the heavy ends to benzene and toluene, particularly benzene, places an impurity into the acetone which is extremely difficult if not impossible to economically remove during the acetone purification. The presence of benzene in product acetone removes certain end use markets from consideration. Therefore, an acetone product with a substantially reduced benzene content is a desirable goal.

This goal has been achieved by removal of the benzene through the method of this invention. Surprisingly it has also been noticed that compounds which deleteriously affect phenol quality according to the sulfonation color test can also be removed from the process by the method of this invention. Previously such compounds had been removed in the phenol purification procedures at a more disadvantageous time, thereby resulting in more product loss and poorer energy utilization. These positive results are achieved with very little loss in overall cumene, the process starting material.

SUMMARY OF THE INVENTION

In accordance with the invention, there is a process for oxidatively preparing phenol and acetone from cumeme including the steps of a. cleaving cumene hydroperoxide to produce a mixture comprising phenol, acetone and side products including heavy residue;

b. separating acetone from phenol and heavy residue;

c. separating the heavy residue from the phenol;

d. treating the said heavy residue at elevated temperature;

e. separating lighter boiling material from heavier boiling material of the heavy residue, said lighter boiling material comprising cumene, α-methylstyrene, and phenol;

the improvement comprising f. separating the said lighter boiling material into two fractions, the lighter fraction comprising the bulk of the benzene and toluene, the heavier fraction comprising the bulk of the phenol, cumene and α-methylstyrene, and g. not recycling into the process streams any significant portion of the said lighter fraction.

A further aspect of the invention is the materials which may be found in the said lighter boiling fraction that adversely affect the phenol quality as measured by the sulfonation color test. These materials generally thought to include lighter boiling carbonyl compounds are separated with the benzene and toluene and may no longer enter the recycle processes in substantial quantity.

DETAILED DESCRIPTION OF THE INVENTION

As stated previously, the conversion of cumene to phenol and acetone is a well known process utilizing individual process steps well known in the industry. The formation of the cumene hydroperoxide by the air oxidation of cumene is performed under standard conditions and the cumene hydroperoxide brought to a higher concentration by stripping unreacted cumene. To this concentrated quantity of cumene hydroperoxide is added a catalytic quantity of sulfuric acid which helps bring about the cleavage of cumene hydroperoxide to phenol and acetone. The phenol and acetone is then separated or "split" usually on the basis of their boiling points. Each of the basic values, phenol and acetone, are then purified according to whatever end use purity is required, usually by distillation.

As in virtually all chemical processes, the yield of the desired phenol and acetone is not one hundred percent. Relatively early in the technology it was realized that the residue initial distillation from the phenol purification or "heavy ends" were relatively rich in materials, for example, dimers and polymers of α-methylstyrene, cumylphenol and the like which would provide cumene, cumene precursors and phenol after an economic "cracking" reaction, see U.S. Pat. No. 2,715,145 incorporated by reference. Some cumene could eventually be recovered and recycled to the initial oxidation reaction. The recovered phenol would eventually join the phenol in the product purification processing stream. The temperature necessary to bring about this decomposition or "cracking" reaction varies according to the composition of the "heavy ends" and the pressure of the reaction; however, generally a temperature substantially above the boiling points of phenol and acetophenone and in the range of from about 200° to 400° C. is employed.

It has been unappreciated until now that the usual cracking conditions are sufficient to not only produce desirable components but are also of sufficient strength to crack the substituted aromatics all the way down to the methyl substituted benzene, toluene, or to remove all substituents from the aromatic molecule and produce benzene. Previously the entire distillate fraction was recycled into the process, the undistilled residue being incinerated. This recycling caused the acetone fraction to be contaminated with benzene and toluene, particularly benzene.

It has now been discovered that the benzene contaminant can be essentially totally removed from product acetone by treating the distillate from the cracker which breaks down the "heavy ends" accompanying the phenol to a further separation. This separation or "topping" is a distillation which separates the benzene and toluene from the higher boiling constituents such as the cumene, α-methylstyrene, and phenol. Such topping is effectively accomplished by passing a relatively small amount of the fluid in the overhead, thereby maintaining a substantial amount of the desired materials in the residue which is recycled. This distillate does not enter the recycle stream and is generally incinerated. Any set of distillation conditions and equipment parameters which can accomplish the goal of removing essentially all the benzene from the cracker distillate in as small a volume as possible can be employed. Such parameters are well known or easily obtainable to one skilled in chemical engineering.

It has additionally been discovered that this topping of the cracker distillate has the further advantage of generally removing from the recycle stream some of the contaminants which deleteriously affect phenol quality as measured by the sulfonation color test. Previously these contaminants were allowed to build up in the phenol distillation train until they had to be removed with a concurrent decrease in product phenol and an increase in steam usage. Removal of these contaminants in the benzene and toluene fraction creates a more efficient process.

A further understanding of the process may be obtained through the study of the FIGURES attached to this specification.

Cumene enters oxidizer, 12, through line 11 and reacts with air brought in through line 7 to form cumene hydroperoxide. The cumene hydroperoxide is transported from the oxidizer through line 17 to the stripper, 24 wherein the cumene hydroperoxide is concentrated to a higher percent with the concomitant removal of unreacted cumene which is drawn off through line 21 and recycled to line 11 for further use. The concentrated cumene hydroperoxide enters the cleavage reactor, 32, through line 29. A catalytic quantity of sulfuric acid is introduced into the cleavage reactor through line 35 and the cumene hydroperoxide cleaved into a mixture of phenol, acetone and by-products. This mixture is then transported through line 39 to the splitter column, 44, wherein the phenol and acetone are split into two streams by distillation, the overhead containing the acetone and lighter boiling by products leaving the column by line 41 for further purification, the phenol and higher boiling by products leaving the splitter in line 47 and entering phenol distillation tower, 56. The distilled phenol leaves the distillation tower in line 53 for further purification. The residue, previously described as "heavy ends" is transported to the cracker, 64, by line 59. In the cracker, the temperature and pressure are adjusted so that the heavy ends are decomposed, the residue being transported to the incinerator by line 67 and the distillate comprising the mixture of cumene, α-methylstyrene and phenol being recycled by line 61 to line 39 where it again enters the splitter column, 44. The cumene, α-methylstyrene and any benzene and toluene present is separated from the phenol in the splitter column and accompanies the acetone for further purification.

Figure 1:
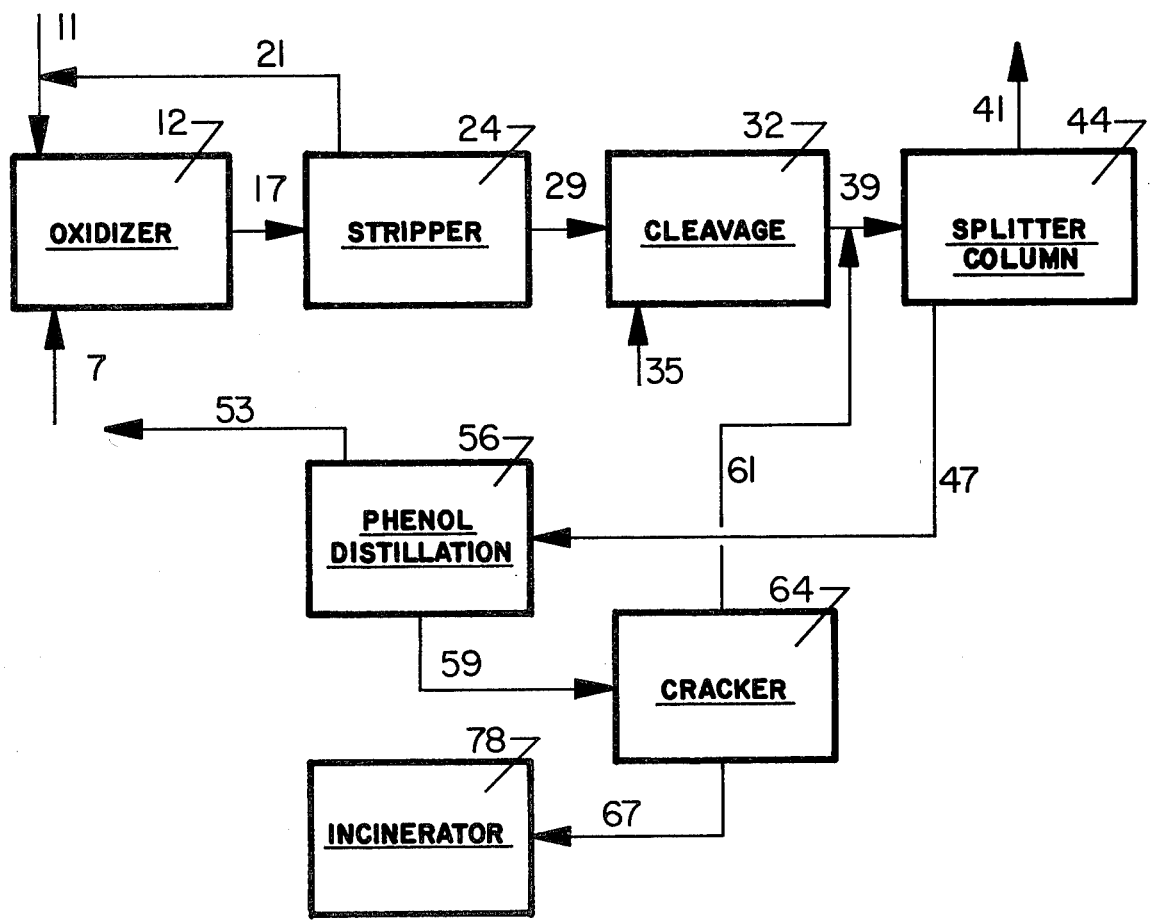
FIG. 1 shows the key steps in the previously practiced process of preparing phenol and acetone from cumene.
Figure 2:
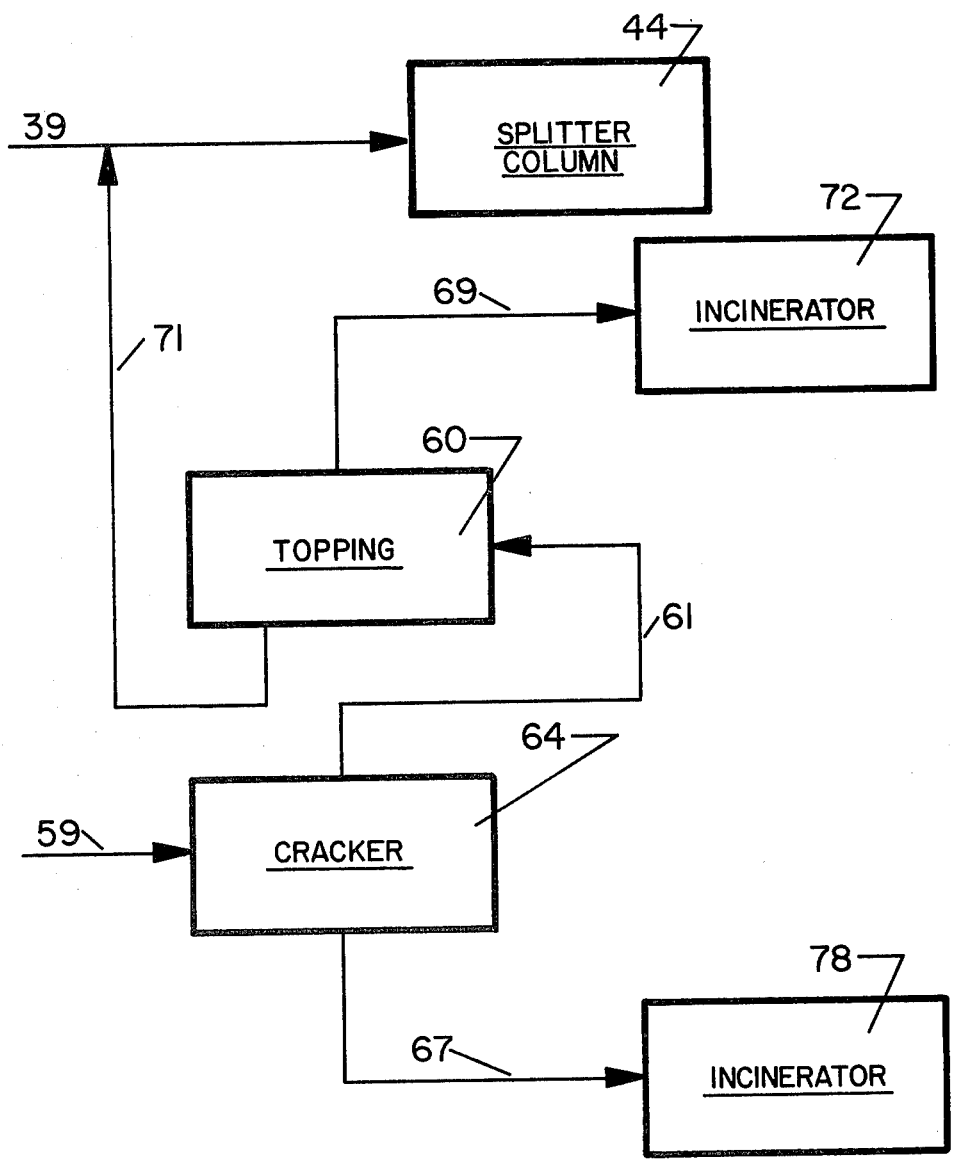
FIG. 2 shows the integration of the topping column of the invention into the previously practiced process steps.

FIG. 2 shows the process of this invention. All process steps are the same through the cracker, 64. However instead of all the cracker distillate being recycled to line 39 by line 61, a topping distillation column, 60, is interposed between the cracker, 64, and line 39. Line 61 feeds the cracker distillate to the topping distillation column, 60, wherein the lighter fraction comprising the benzene and toluene is separated from the heavier fraction comprising cumene, α-methylstyrene and phenol. The lighter fraction is not recycled into the process streams but is preferably transported to incinerator 72 by line 69. The heavier fractions is recycled into the process by transporting through line 71 to line 39.

In the FIGURE the topping distillation is shown between the cracker, 64 and line 39. However it need not be present in this particular location as long as the distillate from the cracker is further distilled to remove the benzene prior to the recycling of the cracker distillate material to the main processing stream. Once present with the acetone it is extremely difficult if not impossible to separate.

It has also been discovered that the lighter fraction also may contain materials which deleteriously affect the phenol quality as measured by the sulfonation color test.

Below are examples of the invention. These examples are intended to illustrate but not narrow the inventive concept disclosed herein.

EXAMPLE 1

The distillate obtained from cracker, 64, of a commercial phenol plant utilizing cumene as a feed stock was analyzed for various components.

The majority of the distillate was cumene and phenol in approximately equal quantities. The remainder of the distillate was divided into various aromatics, some with a boiling point lighter than cumene, others with a boiling point between cumene and phenol. Ketonics were associated with the lighter boiling aromatics. There was 0.1 wt. % benzene in the distillate.

This distillate was then subjected to atmospheric distillation utilizing columns of varying separating capacities and similar operating conditions. The percentage of the cracker distillate which distilled over at the overhead temperature was recorded together with the wt. percent benzene removed from the cracker distillate as well as the wt. percent cumene and phenol remaining in the residue after distillation.

| EQUIPMENT | COLUMN TRAYS | OVERHEAD VAPOR TEMP °C. | SUMP LIQUID TEMP °C. | WT. % DISTILLATE REMOVED | WT. % BENZENE REMOVED | WT. % CUMENE REMAINING | WT. % PHENOL REMAINING |
|---|---|---|---|---|---|---|---|
| A | 5 | 88 | 158 | 3.5 | 69.1 | 97.8 | 100 |
| B | 10 | 89 | 157 | 2.5 | 80.9 | 99.8 | 100 |
| C | 15 | 89 | 159 | 2.5 | 99.5 | 99.2 | 100 |

The data clearly show that benzene can be effectively removed as a contaminant of product acetone by the separation of the benzene by topping the cracker distillate. This removal was accomplished while retaining all the phenol for recovering and virtually all the cumene for effective recycle.

EXAMPLE 2

The vapor overhead of Experiment C of Example 1 was condensed and recovered. It was a bright yellow in color. Various quantities of the recovered overhead were added to a 50 gm. sample of commercial grade phenol suitable for the preparation of bisphenol-A polycarbonate and a sulfonation color test run on each of the samples. The color test procedure was the following:

20 ml. of concentrated $H_2SO_4$ were slowly added over a 5 minute period to 20 ml. of molten phenol held in a test tube in a water batch controlled at 45°–50° C. A golden yellow color development is observed. The mixture is stirred and a portion of the mixture transferred to a 2 cm glass cell. Percent transmission (%T) is read at 532 nm using a Varian Model 210 spectrophotometer or equivalent. The %T value is reported as SAD color.

The lower the purity of the phenol, the more intense is the above color development and the lower the % transmission value (%T). Below are the results:

| EXPERIMENT | VOLUME OVERHEAD ADDED TO 50 gm. OF PHENOL IN μl | % T @ 532 nm |
|---|---|---|
| A | 0 | 93.5 |
| B | 1 | 83.8 |
| C | 5 | 72.0 |
| D | 15 | 43.6 |

The above data clearly shows the negative effect on the phenol quality when the material accompanying the benzene is found in product phenol.

What is claimed is:

1. In a process for oxidatively preparing phenol and acetone from cumene including the steps of
   a. cleaving cumene hydroperoxide to produce a mixture comprising phenol, acetone and side products including heavy residue;
   b. separating acetone from phenol and heavy residue;
   c. separating the heavy residue from the phenol;
   d. treating the said heavy residue at elevated temperature;
   e. separating lighter boiling material from heavier boiling material of the residue, said lighter boiling material comprising cumene, α-methylstyrene, and phenol;

the improvement comprising
   f. separating the said lighter boiling material into two fractions, the lighter fraction comprising the bulk of the benzene and toluene, the heavier fraction comprising the bulk of the phenol, cumene and α-methylstyrene; and
   g. not recycling into the process streams any significant portion of the said lighter fraction.

2. A process in accordance with claim 1 wherein the said lighter fraction contains above about 75 percent of the benzene and toluene found in the said lighter boiling material.

3. A process in accordance with claim 1 wherein essentially all the said lighter fraction is not recycled into the process streams.

4. A process in accordance with claim 1 wherein the heavy residue is cracked at a temperature sufficient to produce significant quantities of benzene and/or toluene.

5. A process in accordance with claim 1 wherein the improvement further comprises the said lighter fraction including materials which deleteriously affect the quality of phenol as measured by the sulfonation color test.

6. A process in accordance with claim 5 wherein the said lighter fraction contains above about 75 percent of the benzene, toluene and materials which deleteriously affect the quality of phenol as measured by sulfonation color test found in the said lighter boiling material.

7. A process in accordance with claim 5 wherein essentially all the said lighter fraction is not recycled into the process streams.

8. A process in accordance with claim 5 wherein the heavy residue is cracked at a temperature sufficient to produce significant quantities of benzene and/or toluene.

* * * * *